(12) United States Patent
Messerschmidt et al.

(10) Patent No.: US 6,230,034 B1
(45) Date of Patent: *May 8, 2001

(54) DIFFUSE REFLECTANCE MONITORING APPARATUS

(75) Inventors: Robert G. Messerschmidt; Mark Ries Robinson, both of Albuquerque, NM (US)

(73) Assignee: Rio Grande Medical Technologies, Inc., Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/324,286

(22) Filed: Jun. 2, 1999

Related U.S. Application Data

(63) Continuation of application No. 08/871,366, filed on Jun. 9, 1997, now Pat. No. 5,935,062, which is a continuation-in-part of application No. 08/513,094, filed on Aug. 9, 1995, now Pat. No. 5,636,633.

(51) Int. Cl.[7] ........................................................ A61B 5/00

(52) U.S. Cl. ............................................................ 600/322

(58) Field of Search ..................................... 600/310, 322, 600/323, 344, 336, 340, 473; 356/446; 250/339.11, 341.8

(56) References Cited

U.S. PATENT DOCUMENTS

| | | | |
|---|---|---|---|
| 3,508,830 | 4/1970 | Hopkins et al. | 356/103 |
| 3,769,974 | 11/1973 | Smart et al. . | |
| 4,655,225 | 4/1987 | Dähne et al. . | |
| 4,661,706 | 4/1987 | Messerschmidt et al. | 250/341 |
| 4,852,955 | 8/1989 | Doyle et al. | 350/1.2 |
| 4,853,542 | 8/1989 | Milosevic et al. | 250/353 |
| 4,859,064 | 8/1989 | Messerschmidt et al. | 356/446 |
| 4,975,581 | 12/1990 | Robinson et al. | 250/339 |
| 5,015,100 | 5/1991 | Doyle | 356/445 |
| 5,019,715 | 5/1991 | Sting et al. | 250/571 |
| 5,051,602 | 9/1991 | Sting et al. | 250/571 |
| 5,224,478 | 7/1993 | Sakai et al. . | |
| 5,355,880 | 10/1994 | Thomas et al. . | |
| 5,379,764 | 1/1995 | Barnes et al. . | |
| 5,452,723 | 9/1995 | Wu et al. . | |
| 5,490,506 | 2/1996 | Takatani et al. . | |
| 5,533,509 | 7/1996 | Koashi et al. . | |
| 5,636,633 | 6/1997 | Messerschmidt et al. . | |
| 5,830,132 | 11/1998 | Robinson | 600/310 |
| 5,935,062 | 8/1999 | Messerschmidt et al. | 600/322 |
| 6,016,435 | 1/2000 | Maruo et al. | 600/316 |

OTHER PUBLICATIONS

Marbach, Ralf, "Measurement Techniques for IR Spectroscopic Blood glucose Determination," (1994) pp. 1–158.

McIntosh, Bruce C. et al., Paper No. 424, 16th Annual FACSS Conference, Oct. 1989.

Korte, E.H. et al., "Infrared Diffuse Reflectance Accessory for Local Analysis on Bulky Samples," *Applied Spectroscopy*, vol. 42, No. 1, Jan. 1988, pp. 38–43.

Marbach R. et al., "Optical Diffuse Reflectance Accessory for Measurements of Skin Tissue by Near–Infrared Spectroscopy," *Applied Optics*, vol. 34, No. 4, Feb. 1, 1995, pp. 610–621.

Primary Examiner—Eric F. Winakur
(74) Attorney, Agent, or Firm—Crompton, Seager & Tufte, LLC

(57) ABSTRACT

An improved method and apparatus for diffuse reflectance spectroscopy. A specular control device is provided that can discriminate between diffusely reflected light that is reflected from selected depths or layers within the tissue. The specular control device permits a spectroscopic analyzer to receive the diffusely reflected light that is reflected from, for example, a first layer or depth within the tissue, while preventing the remaining diffusely reflected light from reaching the spectroscopic analyzer. Furthermore, the specular control device may prevent the specularly reflected light (e.g. surface reflected light) from reaching the spectroscopic analyzer.

17 Claims, 15 Drawing Sheets

DIFFUSE REFLECTANCE MONITORING APPARATUS

CROSS REFERENCES TO CO-PENDING APPLICATIONS

This application is a continuation of U.S. patent application Ser. No. 08/871,366, filed Jun. 9, 1997, now U.S. Pat. No. 5,935,082 which is a continuation-in-part of U.S. patent application Ser. No. 08/513,094, filed on Aug. 9, 1995, now U.S. Pat. No. 5,636,633, issued Jun. 10, 1997.

TECHNICAL FIELD

The present invention relates generally to diffuse reflectance spectroscopy; and more particularly, to an improved method and apparatus for the spectroscopic measurement or analysis of an analyte concentration in human tissue; and still more particularly, to an improved method and apparatus including a specular reflectance control device for use in such a measurement system.

BACKGROUND OF THE INVENTION

The need and demand for an accurate, non-invasive method for determining analyte concentrations in human tissue is well documented. Barnes et al. (U.S. Pat. No. 5,379,764), for example, disclose the necessity for diabetics to frequently monitor glucose levels in their blood. It is further recognized that the more frequent the analysis and subsequent medication, the less likely there will be large swings in glucose levels. These large swings are associated with symptoms and complications of the disease, whose long term effects can include heart disease, arteriosclerosis, blindness, stroke, hypertension, kidney failure, and premature death. As described below, systems have been proposed for the non-invasive measurement of glucose in blood. However, despite these efforts, a lancet cut into the finger is still necessary for all presently commercially available forms of home glucose monitoring. This is believed so compromising to the diabetic patient that the most effective use of any form of diabetic management is rarely achieved.

The various proposed non-invasive methods for determining blood glucose level, discussed individually below, generally utilize quantitative infrared spectroscopy as a theoretical basis for analysis. Infrared spectroscopy measures the electromagnetic radiation (0.7–25 $\mu$m) a substance absorbs at avarious wavelengths. Atoms do not maintain fixed positions with respect to each other, but vibrate back and forth about an average distance. Absorption of light at the appropriate energy causes the atoms to become excited to a higher vibration level. The excitation of the atoms to an excited state occurs only at certain discrete energy levels, which are characteristic for that particular molecule. The most primary vibrational states occur in the mid-infrared frequency region (i.e., 2.5–25 $\mu$m). However, non-invasive analyte determination in blood in this region is problematic, if not impossible, due to the absorption of the light by water. The problem is overcome through the use of shorter wavelengths of light which are not as attenuated by water. Overtones of the primary vibrational states exist at shorter wavelengths and enable quantitative determinations at these wavelengths.

It is known that glucose absorbs at multiple frequencies in both the mid- and near-infrared range. There are, however, other infrared active analytes in the blood which also absorb at similar frequencies. Due to the overlapping nature of these absorption bands, no single or specific frequency can be used for reliable non-invasive glucose measurement. Analysis of spectral data for glucose measurement thus requires evaluation of many spectral intensities over a wide spectral range to achieve the sensitivity, precision, accuracy, and reliability necessary for quantitative determination. In addition to overlapping absorption bands, measurement of glucose is further complicated by the fact that glucose is a minor component by weight in blood, and that the resulting spectral data may exhibit a non-linear response due to both the properties of the substance being examined and/or inherent non-linearities in optical instrumentation.

Robinson et al. (U.S. Pat. No. 4,975,581) disclose a method and apparatus for measuring a characteristic of unknown value in a biological sample using infrared spectroscopy in conjunction with a multivariate model that is empirically derived from a set of spectra of biological samples of known characteristic values. The above-mentioned characteristic is generally the concentration of an analyte, such as glucose, but also may be any chemical or physical property of the sample.

The method of Robinson et al. involves a two-step process that includes both calibration and prediction steps. In the calibration step, the infrared light is coupled to calibration samples of known characteristic values so that there is differential attenuation of at least several wavelengths of the infrared radiation as a function of the various components and analyte comprising the sample with known characteristic value. The infrared light is coupled to the sample by passing the light through the sample or by reflecting the light from the sample. Absorption of the infrared light by the sample causes intensity variations of the light that are a function of the wavelength of the light. The resulting intensity variations at the at least several wavelengths are measured for the set of calibration samples of known characteristic values. Original or transformed intensity variations are then empirically related to the known characteristic of the calibration samples using a multivariate algorithm to obtain a multivariate calibration model.

In the prediction step, the infrared light is coupled to a sample of unknown characteristic value, and the calibration model is applied to the original or transformed intensity variations of the appropriate wavelengths of light measured from this unknown sample. The result of the prediction step is the estimated value of the characteristic in the unknown sample. The disclosure of Robinson et al. is incorporated herein by reference.

Dähne et al. (U.S. Pat. No. 4,655,225) further disclose a method utilizing near infrared spectroscopy for non-invasively transmitting optical energy in the near infrared spectrum through a finger or earlobe of a subject. Dähne also disclose measuring reflected light energy to determine analyte concentration. The reflected light energy is further stated as comprised of light reflected from the surface of the sample and light reflected from deep within the tissue. It is the near infrared energy diffusely reflected from deep within the tissues that Dähne disclose as containing analyte information, while surface reflected light energy gives no analyte information and interferes with interpreting or measuring light reflected from deep in the tissue. The present invention is directed to an apparatus for improved measurement of diffusely reflected light, while eliminating the effects of surface reflected light and other light not reflected from deep within the tissue.

Reflectance spectroscopy is known in other non-medical applications. In general, such spectroscopy is concerned with identification of the chemical structure of the sample through the use of reflected information. Diffuse reflectance spectroscopy is also generally known, and is widely used in the visible and near-infrared regions of the light spectrum to study materials such as grains and other food products.

In broad terms, diffuse reflectance spectroscopy utilizes the fact that the sample materials will tend to scatter light in a more or less random fashion. A fraction of the light will eventually be scattered back from the sample and collected by a detector to provide a quantitative or qualitative representation of the sample.

In infrared spectroscopy it is often desirable to use the mid-infrared region of the spectrum. The fundamental vibrational absorptions described earlier are strongest here, in the fundamental region. The goal of infrared spectroscopy sampling is often to prepare a sample so that it may be analyzed with this mid-infrared light. Reflectance spectroscopy is one very popular way of making a sample compatible with mid-infrared light. If a sample is too thick to get any light through in transmission, often a result can be obtained by reflectance. Reflectance spectroscopy is complicated however, by the fact that there is more than one optical phenomenon occurring in this mode.

Reflectance of light from a sample can be largely divided into two categories, diffuse reflectance and specular reflectance. The specular reflectance of a sample is the light which does not propagate into the sample, but rather reflects "like a mirror" from the front surface of the sample. This component contains information about the sample at the surface. If the material is homogeneous, this surface reflection can be related to the bulk. While the specular component does not physically appear much like an absorbance spectrum, it can be related to the absorbance spectrum of the bulk material through a transformation called the Kramers-Kronig transformation. Still, most experts agree that the diffuse component is much more useful for sample qualification and quantification than is the specular component. There has been a lot of effort, by the applicants and by others, to enhance the diffuse component, and de-emphasize the specular component and to essentially cause the reflectance spectrum to be more transmission-like.

Generally these efforts fall largely into three categories: optical discrimination against specular, mechanical discrimination, and secondary methods of sample preparation designed to minimize specular. A fourth, non-independent approach is to move away from the mid-infrared region in order to relax the sample preparation requirements. By moving to the near-infrared or visible region of the spectrum, the vibrational spectroscopy becomes more blunt and imprecise, but often this can be made up for by the improvements observed in the quality and signal-to-noise ratio of the data obtained because of improved sampling ability, more appropriate path length, and better discrimination against specular reflectance. This approach is especially useful when quantitative information is desired.

Most experts would agree that the diffuse component is desirable, and even essential, if the sample material is layered or non-homogeneous. The specular component will largely contain information about the surface of the sample and not about the bulk. Nevertheless, U.S. Pat. No. 5,015,100, issued May 14, 1991 to Walter M. Doyle, describes an example of the specular approach. The specular component of the light is significantly wavelength dependent, and contains information about the complex refractive index of the material under test. This complex refractive index contains an imaginary term which relates to the absorption coefficient of the material.

Doyle indicates that the potential utility of specular reflectance spectroscopy is well-known to those of skill in the art and points out that mathematical expressions, namely the Kramers-Kronig relation, can be used to convert measured reflectance spectra into absorbance spectra. These calculated spectra are then useful for identifying samples by comparison with existing libraries of absorbance spectra. However, the work of the prior art has not been used for quantitative measurements such as the composition analysis of tissue fluids. In fact, it would perform poorly for this purpose, since there is little tissue fluid information at the surface of the skin. The diffuse component must be used.

Paper No. 424, presented at the 16th Annual FACSS Conference in October, 1989, by Doyle and McIntosh, concluded that the Kramers-Kronig relations could not be used to obtain accurate absorbance spectra from reflectance data unless the equations used were modified to take into consideration polarization and angle of incidence, or unless the experimental apparatus provided radiation which approximated the conditions at normal incidence.

The Doyle patent reference describes the use of apparatus in a specular reflectance system in which the analytical radiation reflected by the sample approximates the conditions existing at normal incidence, and proposed a solution by ensuring essentially equal contributions from rays polarized parallel to the plane of incidence and from rays polarized perpendicular to the plane of incidence. Doyle teaches that a semi-transparent beamsplitter used in such an apparatus would achieve the desired polarization balance, but would sacrifice radiation efficiency because of losses in pre-sample transmission, post-sample reflection, and absorbance loss in the beamsplitter. The Doyle reference then described a system of improved radiation efficiency utilizing a split field beamsplitter having a surface area divided into an uneven plurality of reflecting blades and open transmitting areas.

U.S. Pat. No. 4,852,955 also issued to Doyle, describes a system which obviates the problem of limited beamsplitter efficiency by using a 100% reflecting mirror intercepting half of the system aperture, and arranging for the illuminating and outgoing beams to use opposite halves of the aperture. However, the use of the split field beamsplitter of this reference involves a distribution of incident radiation which is asymmetrical with respect to an axis normal to the sample surface. As a result, there is no assurance that the p and s polarization states will be balanced when the suggested beamsplitter is in use.

The limitations of Doyle's prior art are clear. Specular reflectance is only useful when the bulk material is adequately represented by surface composition. When this is not the case, such as when performing non-invasive blood analyte measurements, this methodology will give a spurious result.

Optical means have also been used to separate diffuse and specular components. A recent example is described by Ralf Marbach in his PhD. thesis entitled "Messverfahren zur IR-spektroskopishen Blutglucose bestimmung" (English translation: "Measurement Techniques for IR Spectroscopic Blood Glucose Determination"), and published in Duesseldorf in 1993. Marbach employs an optical discrimination system quite similar in principle to that used by Harrick Scientific Corp. in the Praying Mantis diffuse reflectance instrument first introduced in 1980. The concept here is that the specular light reflects from a sample with an angle equal and opposite to the angle of incidence to the surface normal. Using this fact, it is a simple matter to collect light only outside the input collection angle. Marbach and Harrick then limit the input angle to a small range, so that a larger range of output angles may be used for collection.

Note that there is a limited region of space over which light can be launched into and collected from a sample. In terms of solid angle, for a planar surface sample, this working volume can be stated to be $2\pi$ steradians in solid angle. In the Harrick device, a small and equal solid angle is subtended by the input and the output optics. Less than $\frac{1}{2}$ $\pi$ steradians is subtended by either the input or the output optic. This leads to an efficiency of less than 50% of the available solid angle. Another critical factor in collecting diffusely reflected light is the directionality of the collected light. Many samples, including the tissue samples required for non-invasive measurements are quite forward scattering. That is to say that a scattered photon will change only a small angle in direction after a scattering event. The Harrick device requires a photon to deviate through a large angle before it can be collected by the output optics. This poor performance in the presence of sample anisotropy and the relatively low efficiency are severe problems with the Harrick device.

The Marbach device improves on the Harrick device in a number of ways. First, the total volume available for input and collection of light approaches $2\pi$ steradians which is the theoretical limit. This is accomplished by allowing 360° azimuthal angular subtense for both the input and output light. Second, the forward directionality of scatter is taken into account. Rays which deviate only a few degrees in angle can be collected. The downfall of this approach is that the input and output optical systems are completely unmatched in terms of magnification. Any diffuse reflectance system must work in concert with the source and the detector of the system.

Since detectors in the near-infrared region of the spectrum get noisier when they get bigger, it should be a goal to make the detector as small as possible. A bright compact source is also advantageous. In the Marbach system, the image of the source is very much magnified relative to the image of the detector in the sample plane. This means that the source energy density which can be imaged onto the detector is limited. In addition, the collected energy from the sample is demagnified as it travels to the detector. Again, energy efficiency is compromised. An ideal situation would leave the input and output magnifications equal.

Another important limitation of the Marbach design relates to the choice of angles for input and output. Real optical systems are good at imaging with large f/numbers. Small f/number systems, especially with large field stop diameters, tend to image poorly. Marbach notes this fact in his thesis. In his design, the prime, large f/number, near-normal space is all reserved for input light, and the non-ideal near-grazing light is used for output. It is quite conceivable that the device would work better if used "backwards" from the mode employed by Marbach, where the source site and the detector site would be switched. The device described in this application provides an even better solution.

Another method of eliminating specular contribution to a diffuse reflectance spectrum is to modify the sample itself to reduce its propensity to reflect specularly. One way to accomplish this is to dilute a powdered sample in a non-absorbing matrix material with a low refractive index. The low index matrix will have a low amount of specular component and will mitigate the specular problem. Unfortunately, the goal of non-invasive analysis does not allow for modification of the sample, and so in the field of use described here, these dilution methods are not an option.

Finally, an apparatus for mechanically discriminating against specular reflectance is shown in U.S. Pat. No. 4,661,706, issued Apr. 28, 1987, to Robert G. Messerschmidt and Donald W. Sting. Messerschmidt et al. demonstrate that the specular and the diffuse component of reflected light can be separated mechanically, taking advantage of the fact that the specular component emanates from the surface of the sample. A blade-like device, or blocker, "skims" the specular light before it can impinge on the detector.

Messerschmidt et al. teach that a "thin" blocker is essential to maximizing the efficiency of the system, and minimizing the distortion of the output spectrum. More particularly, Messerschmidt et al. state that to obtain the maximum efficiency and the closest approximation to the Kubelka-Munk relationship, a thin blocker device should be used having an edge that is a fraction of the optical depth of the sample. A thicker blocker, Messerschmidt et al. explain, will remove energy that penetrates only a short distance into the sample before reflecting, and thus may have a catastrophic effect on the efficiency when used with a sample having a shallow optical depth.

Messerschmidt et al. also state that a thick blocker may introduce spectral distortions caused by energy that is once reflected by the sample to the lower surface of the blocker and again reflected from the blocker to the sample before energy escapes from the far side of the blocker. This is problematic, according to Messerschmidt et al., because the energy reflected from the lower surface of the blocker will acquire the reflectance spectral features of the blocker itself and thus distort the output spectrum.

Applicants have discovered that the "thin" blocker approach of Messerschmidt et al. suffers from a number of limitations, some of which are discussed below. First, the "thin" blocker approach does not provide any discrimination between the diffusely reflected energy that is reflected from various depths within the sample. This limitation is of particular importance when the sample is layered or otherwise non-homogeneous, and only a selected set of the layers contain the desired information. Second, the "thin" blocker of Messerschmidt et al. may not perfectly conform to a rough surface of a sample. This can cause locations where the light effectively leaks or pipes under the blocker without interacting with the sample, thereby distorting the resulting output spectrum.

SUMMARY OF THE INVENTION

The present invention overcomes many of the disadvantages of the prior art by providing a method and apparatus for improved measurement of diffusely reflected light for analyte concentration determination within human tissue. The present invention incorporates a specular control device that can discriminate between diffusely reflected light that is reflected from selected depths or layers within the tissue. The specular control device permits a spectroscopic analyzer to receive the diffusely reflected light that is reflected from, for example, a first layer or depth within the tissue, while preventing the remaining diffusely reflected light from reaching the spectroscopic analyzer. Furthermore, the specular control device may prevent the specularly reflected light (e.g. surface reflected light) from reaching the spectroscopic analyzer.

The specular control device may include an immersion lens that has a flat bottom surface and a semi-circular shaped top surface. The flat bottom surface is positioned on the surface of the tissue sample. A blocker blade is positioned within the immersion lens, and extends substantially perpendicular to the surface of the tissue sample. In a preferred embodiment, the blocker blade divides the immersion lens into approximately two equal halves, and extends downward to the flat bottom surface of the immersion lens. The blocker blade is constructed to either reflect or absorb light having a wavelength in the range of the expected specularly and diffusely reflected light.

The incident light is directed to one of the two equal halves of the immersion lens. The blocker blade substantially prevents the incident light from traveling to the other half of the immersion lens. The immersion lens directs the incident light to the tissue sample, and in some embodiments, focuses the light on an illuminated spot on the surface of the tissue sample. A first portion of the incident light may be specularly reflected from the surface of the sample. A second portion of the light may enter the sample, and be diffusely reflected by the material within the sample. The diffusely reflected light is typically reflected at various depths within the sample.

The blocker blade may have two opposing surfaces including a front surface and a back surface, with a thickness defined therebetween. The thickness may be defined such that the blocker blade discriminates between light rays that are diffusely reflected from a first depth within the tissue from those light rays that are diffusely reflected from a second depth. The thickness of the blocker blade is dependent, at least in part, on the angle of incidence and the spot size of the incident light rays on the tissue. The thickness of the blocker blade is made sufficiently thick to substantially prevent those light rays that are diffusely reflected from a selected depth or layer within the sample from reaching the spectroscopic analyzer.

The present invention is particularly useful for obtaining a diffuse reflectance spectra from human tissue for the non-invasive measurement of blood analytes such as glucose. It is known that human skin typically includes an outer epidermis layer and an inner dermis layer. The epidermis layer contains very little or no blood, and thus the corresponding diffusely reflected light reflected from the epidermis layer typically contains little or no glucose information. Thus, the diffusely reflected light from the epidermis layer tends to contaminate the desired spectrum of the diffusely reflected light from the information rich dermis layer. By preventing the diffusely reflected light from the epidermis layer from reaching the spectroscopic analyzer, a information rich spectrum from the dermis layer can be obtained and analyzed. Thus, Applicants have discovered that it is desirable to exclude the diffusely reflected light rays that are reflected from the epidermis layer.

To achieve discrimination, the back surface of the blocker blade may be laterally spaced a distance from the illuminated portion of the tissue sample such that the light rays that are diffusely reflected from the epidermis layer are substantially prevented from reaching the spectroscopic analyzer. The front surface of the blocker blade may be positioned directly adjacent the illuminated portion of the tissue sample, within the illuminated portion, or laterally spaced toward the back surface relative to the illuminated portion.

In addition to the above describe advantages, the thick blocker blade of the present invention may substantially prevent the specularly reflected component of light from reaching the spectroscopic analyzer, even when the surface of the sample is not perfectly flat. One such sample is human skin. It is known that the surface of human skin is relatively rough and moderately rigid. Because the present invention provides a thick blocker blade, the leakage of light between the surface of the skin and the blocker blade may be reduced. This may improve the quality of the resulting spectrum that is provided to the spectroscopic analyzer.

Finally, a method for obtaining a diffuse reflectance spectra from human tissue for the non-invasive measurement of blood analytes is contemplated. The method comprising the steps of: (a) generating infrared energy; (b) directing the infrared energy to the tissue; and (c) collecting the infrared energy that is reflected from a first depth and rejecting the infrared energy that is reflected from a second depth.

BRIEF DESCRIPTION OF THE DRAWINGS

Other objects and many of the attendant advantages of the present invention will be readily appreciated as they become better understood by reference to the following detailed description when considered in connection with the accompanying drawings, in which drawings like reference numerals designate like parts throughout the figures thereof and wherein.

DETAILED DESCRIPTION OF THE PREFERRED EMBODIMENTS

The present invention is directed to an improved apparatus for spectrographic analysis or measurement of an analyte concentration. In preferred embodiments, the apparatus is utilized for measuring analyte concentrations in tissue of human patients, more particularly, the invention is focused on analyzing glucose concentration in the tissue. The basis for measurement is diffusely reflected light returning from the tissue sample after being illuminated by a wide-band near-infrared energy source.

Figure 1:
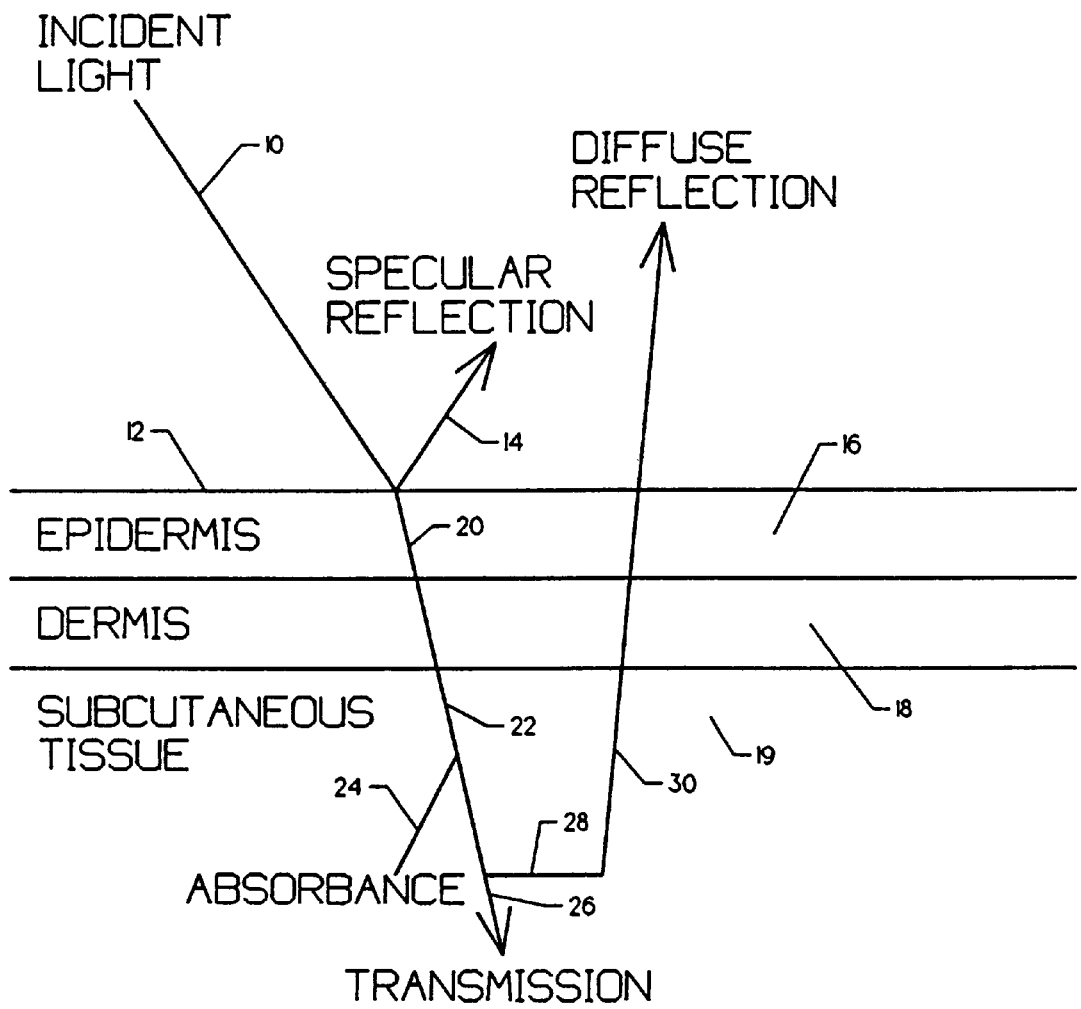
FIG. 1 is a simplified schematic showing the alternative responses to light incident on an analyte-containing tissue, including specular reflection, diffuse reflection, absorption and transmission.

Referring first to FIG. 1, a schematic representation of light energy incident on an analyte-containing tissue sample is depicted. As depicted in the simplified representation, a tissue sample 12 includes an upper layer or epidermis 16, a middle layer or dermis 18 and subcutaneous tissue 19. Incident light 10 illuminates the tissue sample 12, wherein portions of the light energy may be transmitted through the tissue sample, resulting in transmitted light 26 exiting the opposing side of the tissue sample. Alternatively, a tissue sample may absorb a portion of the light energy, resulting in absorbed light energy 24 as heat. A third phenomena includes specular reflection 14 of a portion of the incident light 10. Finally, a portion of the light energy can be diffusely reflected 30.

The diffusely reflected light 30 undergoes several refractions due to contact with the various components within the tissue sample. Eventually a portion of the diffusely reflected light energy 30 returns to the surface of the tissue sample 12 and exits back through the skin surface to the measuring device. Thus, both specular reflected light 14 and diffuse reflected light 30 combine and are directed back toward the instrument of the present invention.

Of the reflected light, only the diffusely reflected light 30 contains analyte or glucose information. The light, which is specularly reflected, contains information on the avascular epidermis, but does not contain glucose information. Thus, the goal of the present invention is to utilize only the diffusely reflected light 30 for analysis by separating such light from the specularly reflected light 14. Specularly reflected light 14 can be viewed as contamination light as it does not contain the necessary information for analysis.

Applicants have found that the problems associated with diffuse reflectance sampling of tissue can be minimized by the distribution of the input and output optics based on center symmetry. In a center symmetry configuration, the light rays 10 are focused onto the tissue sample 12 by an optical system, incorporating lenses. It has been found with this embodiment, the light rays which are specularly reflected off the surface of the tissue 12 exit the optical system on the opposite side of the beam focus. Any light ray entering the system and undergoing specular reflectance exits the system on the opposite side of the center focus.

Figure 2:
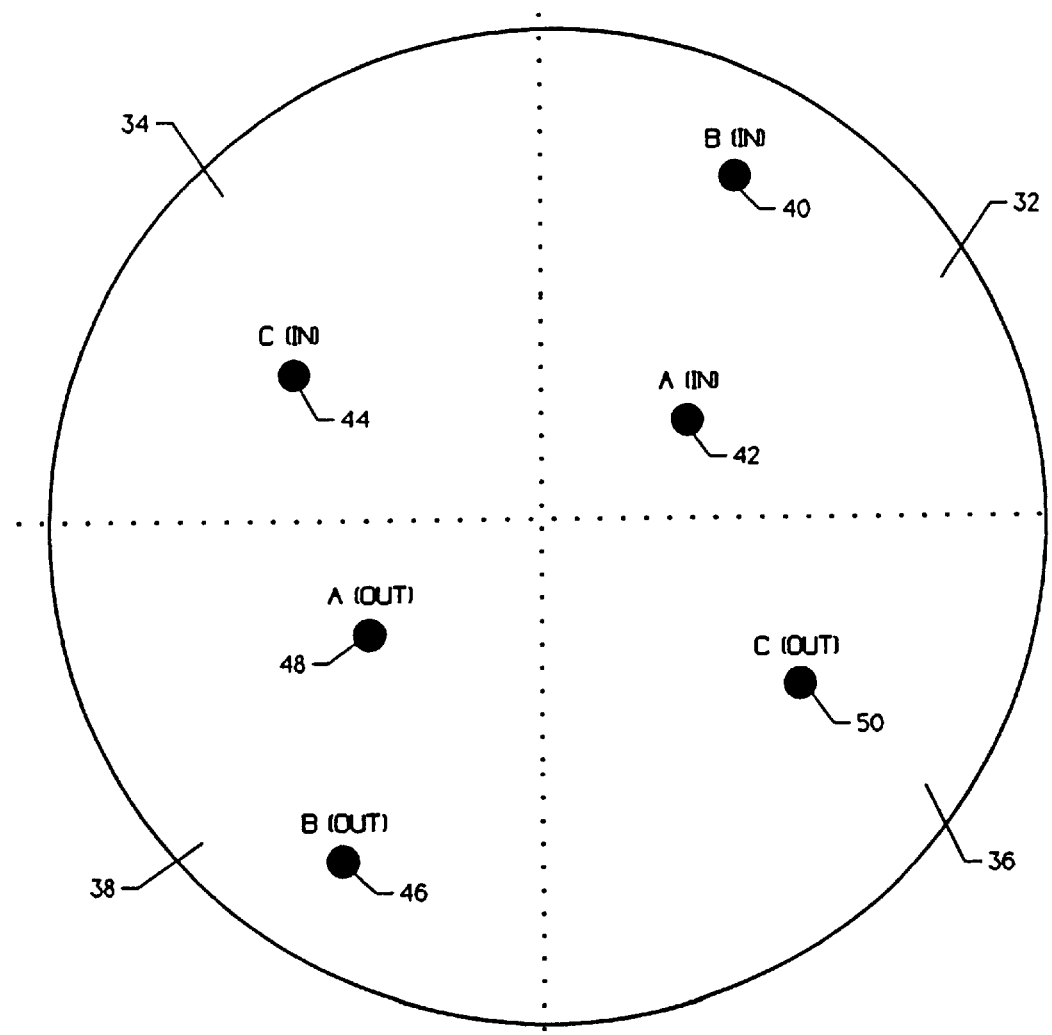
FIG. 2 is a schematic representation of the effect on specular reflectance utilizing input and output rays symmetric about a center focus.

Referring now to FIG. 2, a schematic diagram is presented which illustrates the concept and effect on light rays passing through the lens system, which focuses the beam. As depicted in FIG. 2, light rays A, B, and C are depicted as passing through a generally circular transparent plate divided into four quadrants about the center point. The quadrants include first quadrant 32, second quadrant 34, third quadrant 38 and fourth quadrant 36. As represented, input light energy A 42 is incident on and passes through the plate in the first quadrant. Due to center point symmetry, the output light energy A 48 due to specular reflectance returns through the plate in the third quadrant. Likewise, input light energy B 40 is also incident on the first quadrant 32. Output light energy B 46, which is the result of spectral reflectance exits the third quadrant 38. Similarly, input light energy C 44, which is incident on the second quadrant 34, has a component of specularly reflected light which exits from the fourth quadrant 36 as indicated as output light energy C 50.

Figure 3:
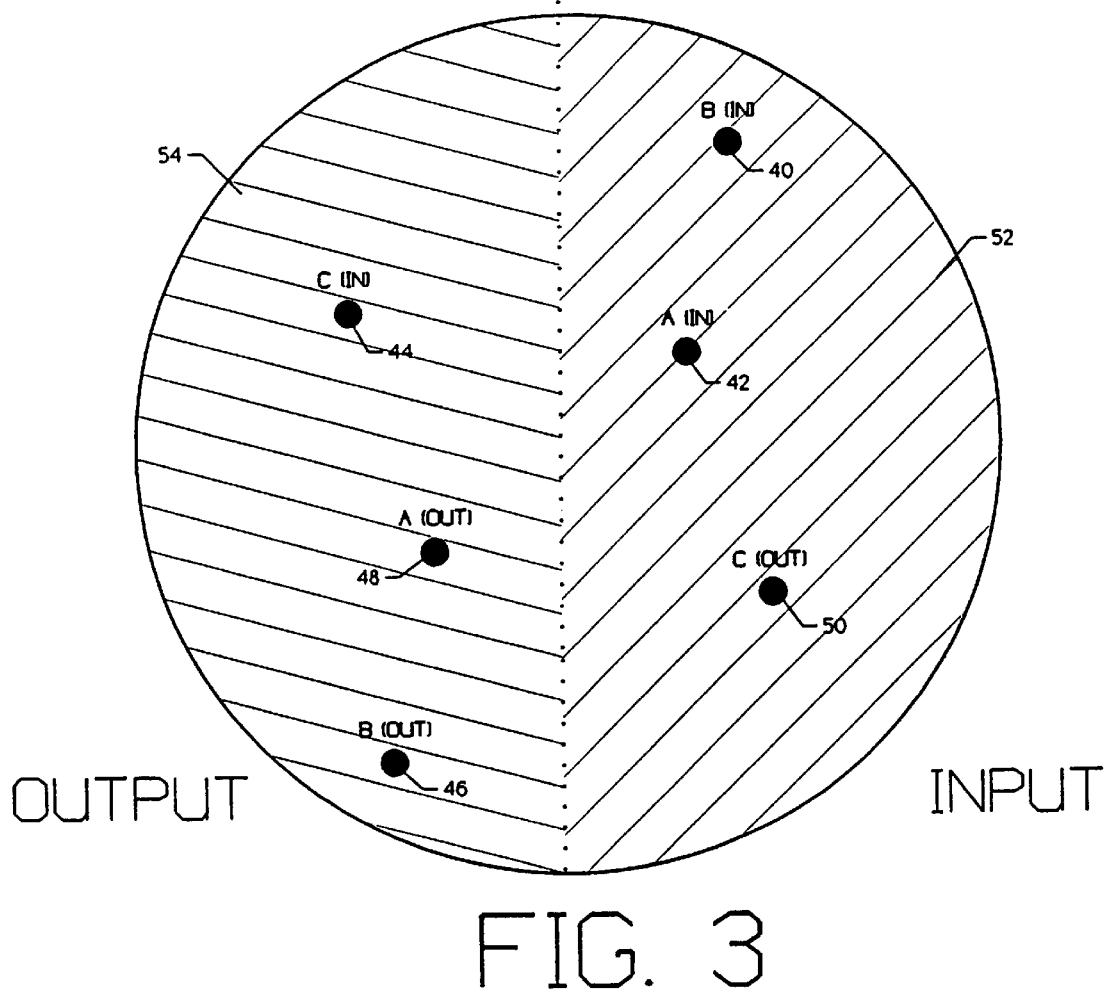
FIG. 3 depicts a typical single mirror optical configuration for reflectance sampling, wherein the optical beam is divided into an input and output side about a single center line.

In contrast to the concept of center point symmetry, a typical single mirror optical configuration for reflectance sampling includes an optical beam divided into an input and an output side about a single center line. This configuration is depicted in FIG. 3. Again, a generally circular plate having an input side 52 and an output side 54 is depicted. The sides are divided by a center line passing through the diameter of the plate. Input rays A 42, B 40 and C 50, which pass through the plate, have specularly reflected components or output light energy A 48, B 46 and C 44, which are actually sampled by the output optics and will be seen by any detector.

Figure 4:
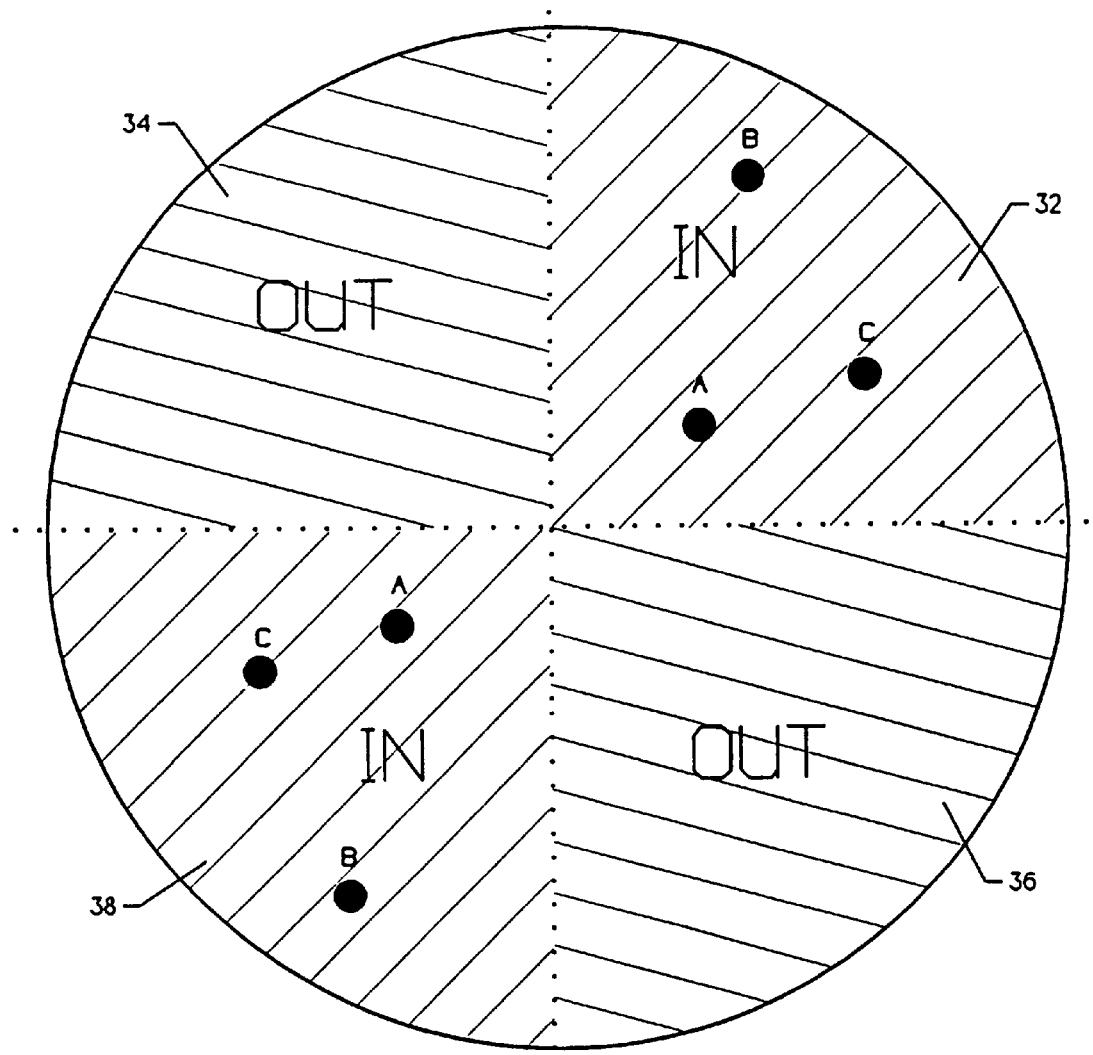
FIG. 4 is a schematic representation of the elimination of specularly reflected light utilizing four quadrants.

Applicants have found that the problems associated with specular reflectance can be eliminated by designing a specular control device incorporating the concepts of center point symmetry as depicted in FIG. 1 to overcome the problems with standard single mirror optical configurations for reflectance sampling. Now referring to FIG. 4, a generally circular plate divided into four quadrants is depicted. With the configuration of FIG. 4, the first quadrant 32 and third quadrant 38 are defined as input quadrants. The second quadrant 34 and fourth quadrant 36 are defined as output quadrants. With this embodiment, the light energy source is incident on the circular plate. However, the input quadrants allow the light energy to pass through, while the output quadrants are opaque. Thus, only light incident on the input quadrants passes through the specular control device to contact the tissue sample.

Light reflected from the tissue sample, including both specularly reflected light and diffusely reflected light is incident upon the opposite side of the specular control device. However, as explained for FIG. 1, all of the specularly reflected light returning from the tissue sample will be incident upon the first or third quadrants 32, 38 and will pass back through these openings. In contrast, a quantity of diffusely reflected light will be incident upon the second quadrant 34 and fourth quadrant 36 without any interfering specular reflection. The diffusely reflected light can then be reflected from the surface of the second and fourth quadrants 34, 36 and directed to the analyzer. In this way only the diffusely reflected light is analyzed.

Figure 5:
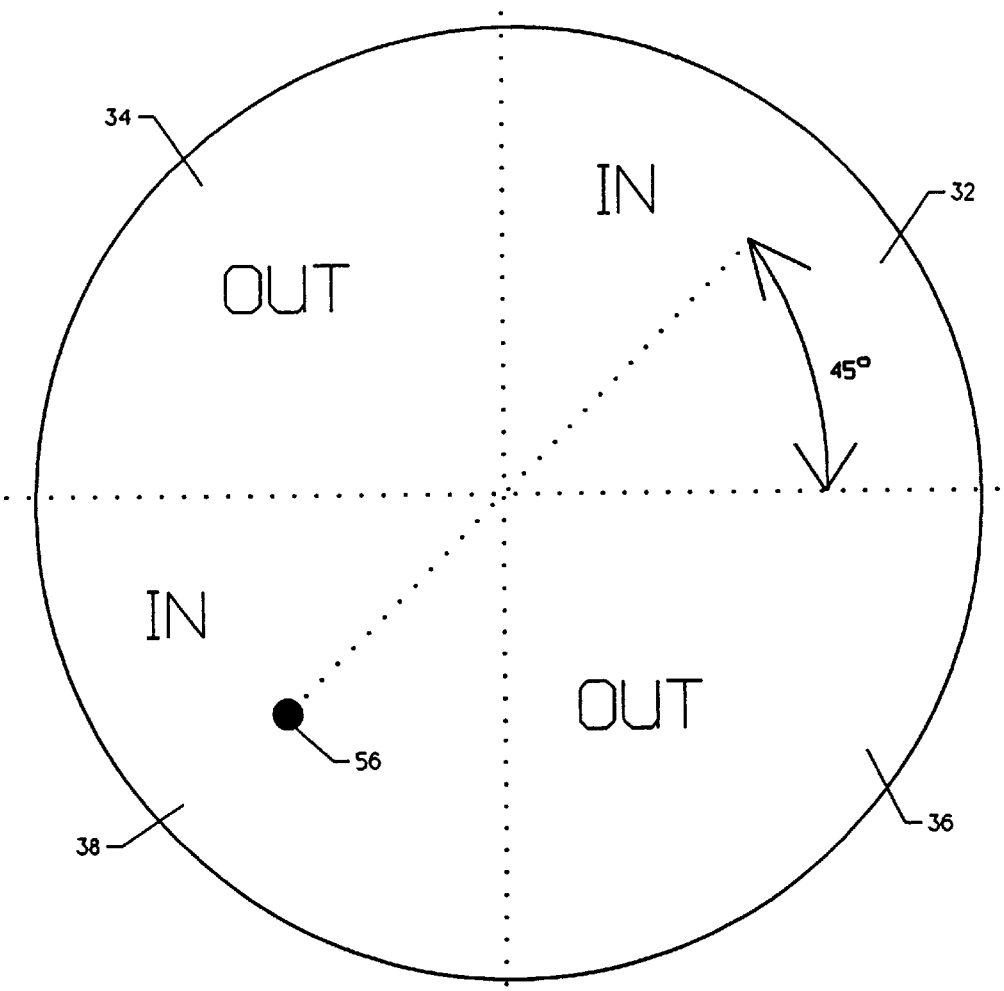
FIG. 5 is a schematic representation of directional change required for diffuse reflected light energy to reach the analyzer.
Figure 6:
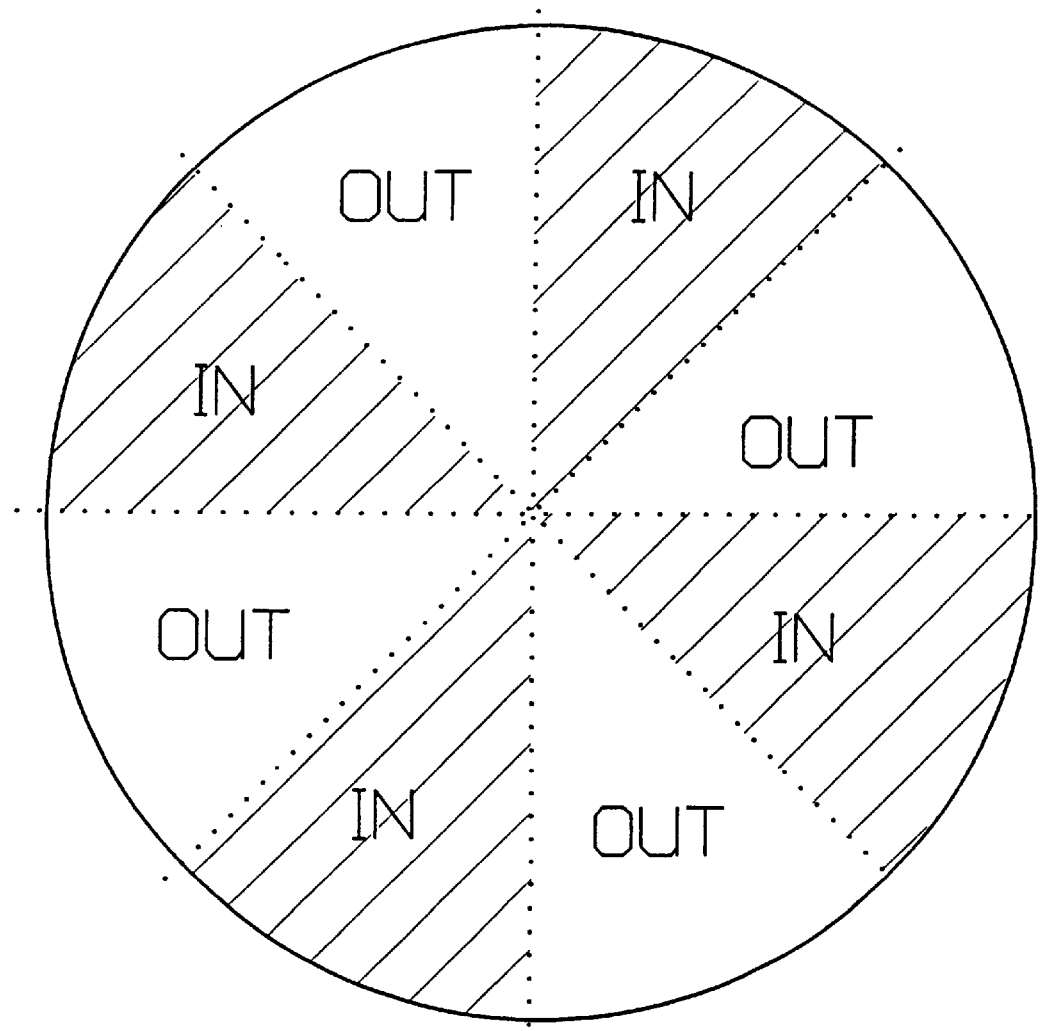
FIG. 6 is a schematic representation of a specular control device incorporating eight quadrants.
Figure 7:
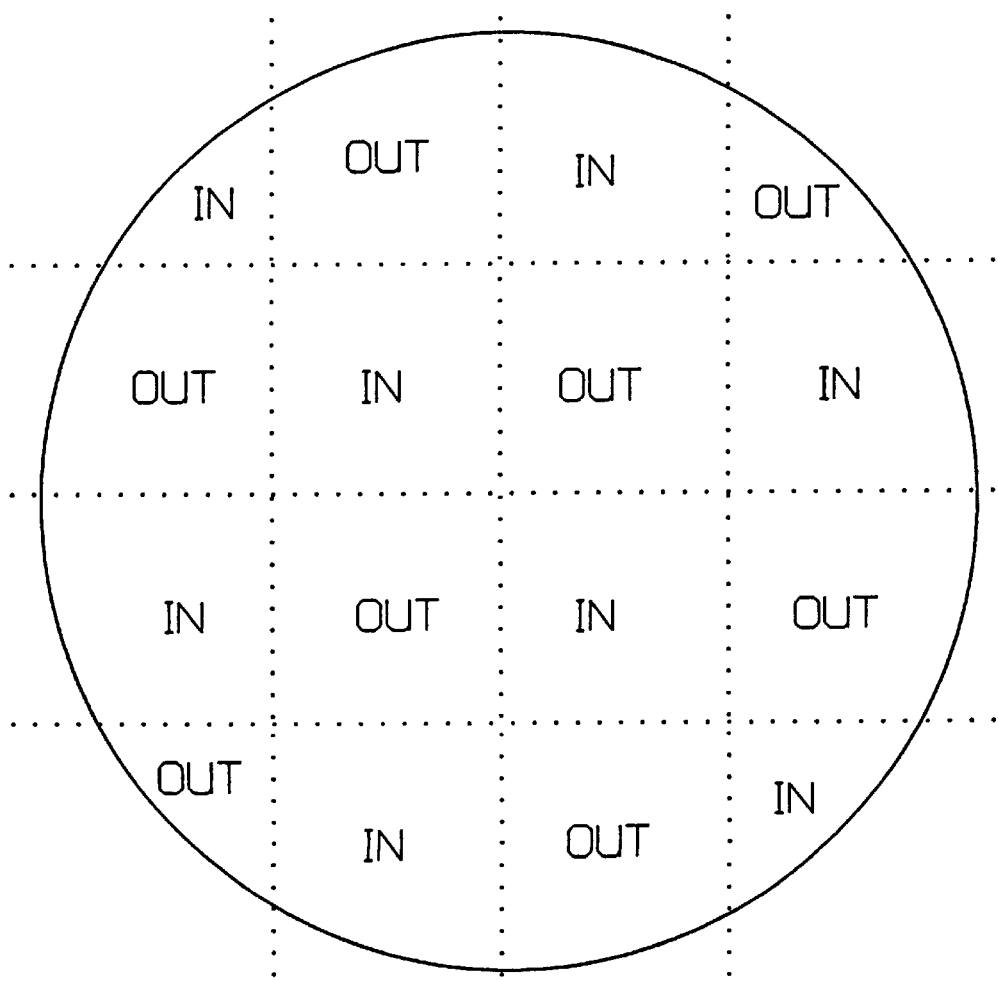
FIG. 7 is a schematic diagram of an alternative specular control device utilizing generally rectangular symmetric quadrants.

As shown in FIG. 5, the diffusely reflected portion of a light ray 56 would have to undergo a change in direction of at least 45 degrees before it could be collected by the output optics. It is recognized that the number of photons which would successfully complete this directional change without absorbance will be less than those that can successfully undergo a smaller directional change. Applicants have recognized that the efficiency of the optical system could be improved by further dividing the optical beam into numerous symmetrically based input and output sections. One such alternative embodiment is depicted in FIG. 6. In FIG. 6, the optical beam is divided into eight separate wedge shaped quadrants about the center point. In the eight quadrant configuration, a light ray located in the center of an input quadrant would have to undergo a directional change of only 22.5 degrees. Applicants recognize that the number of quadrants can be further increased. Alternatively, as depicted in FIG. 7, the optical beam can be divided into 16 generally square quadrants which are also symmetrical about the center point.

Figure 8A:
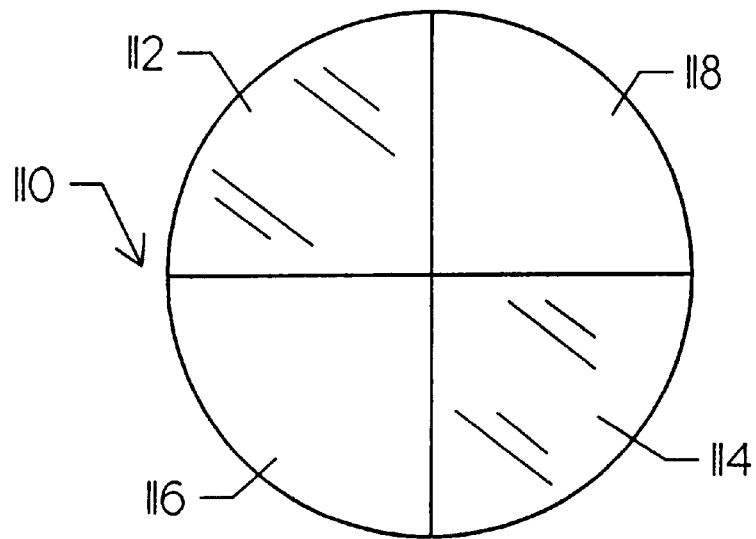
FIG. 8A is a plan view showing a first embodiment of the specular control device.

FIG. 8A discloses a specular control device indicated generally at 110. The surface of specular control device 110 is divided into an even numbered plurality of sections, here shown as open sections 116 and 118, and reflective sections 112 and 114. Open sections 116 and 118 are intended to pass or transmit any beam of light which is incident to the surface of specular control device 110.

In contrast, reflecting sections 112 and 114 are intended to block the incident beam and reflect portions of it to a predetermined site.

In the embodiment of FIG. 8A, each of sections 112, 114, 116 and 118 are of equal size and thus the total surface area of the open sections 116 and 118 is equal to the total surface area of reflecting sections 112 and 114. Further, each of reflecting sections 112 and 114 is situated between a pair of open sections 116 and 118; and, similarly, each of open sections 116 and 118 is located between a pair of reflecting sections 112 and 114. Finally, each reflecting section such as 112 is opposite to another reflecting section such as 114; and, each open section such as 116 is opposite to another open section such as 118.

Figure 8B:
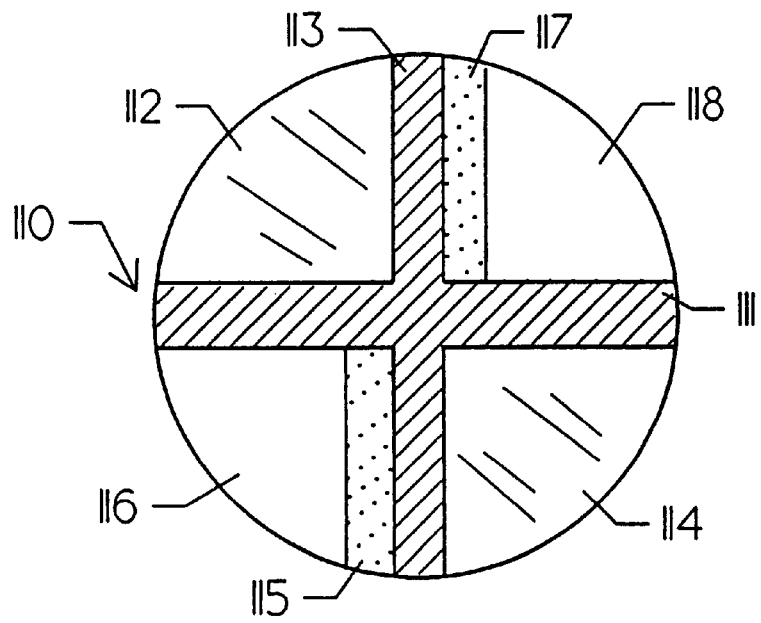
FIG. 8B is a plan view of a second embodiment of the specular control device.

Referring now to FIG. 8B, there is shown another embodiment of the apparatus of FIG. 8A. In FIG. 8B, specular control device 110 is again divided into a plurality of reflecting sections 112 and 114, and open sections 116 and 118. Each reflecting section such as 112 and 114 is situated between a pair of open sections 116 and 118, and similarly each of open sections 116 and 118 is situated between a pair of reflecting sections such as 112 and 114. Each reflecting section is opposite to another reflecting section, and each open section is opposite to another open section.

In FIG. 8B, there is also shown a set of opaque spacers 113 and 111 located along the borders between each of sections 112, 116, 114 and 118. The effect of spacers 111 and 113 is to achieve a more precise definition between the analytical beam sent to illuminate a sample and the data beam reflected from the sample. The opaque spacing between the reflecting and open sections achieves this desired improvement by, for example, preventing cross talk in the various adjacent sections from transmitted and reflected light beams.

When opaque spacers 111 and 113 are utilized along the diameters of a circular specular control device surface such as 110, they result in equal division of the remaining surface area between reflecting sections 112 and 114 and open sections 116 and 118. As it may be desirable for the analysis of certain samples to have the reflecting sections surface area unequal to the open sections surface area, this is shown accomplished in FIG. 8B by the addition of opaque spacers 115 and 117. For purposes of description, opaque area 115 has been shown as added to opaque spacer 113 to decrease the surface area of open section 116; and, similarly, opaque area 117 has been added to opaque spacer 113 to decrease the surface area of open section 118.

In the embodiment shown in FIG. 8B, in a system where the source analytical beam is transmitted through open areas 116 and 118, and the diffuse reflection from a sample is reflected by sections 112 and 114 to a detector, it will be apparent that though the addition of opaque sections 115 and 117 will decrease the percentage of the source beam which illuminates the sample.

Figure 9:
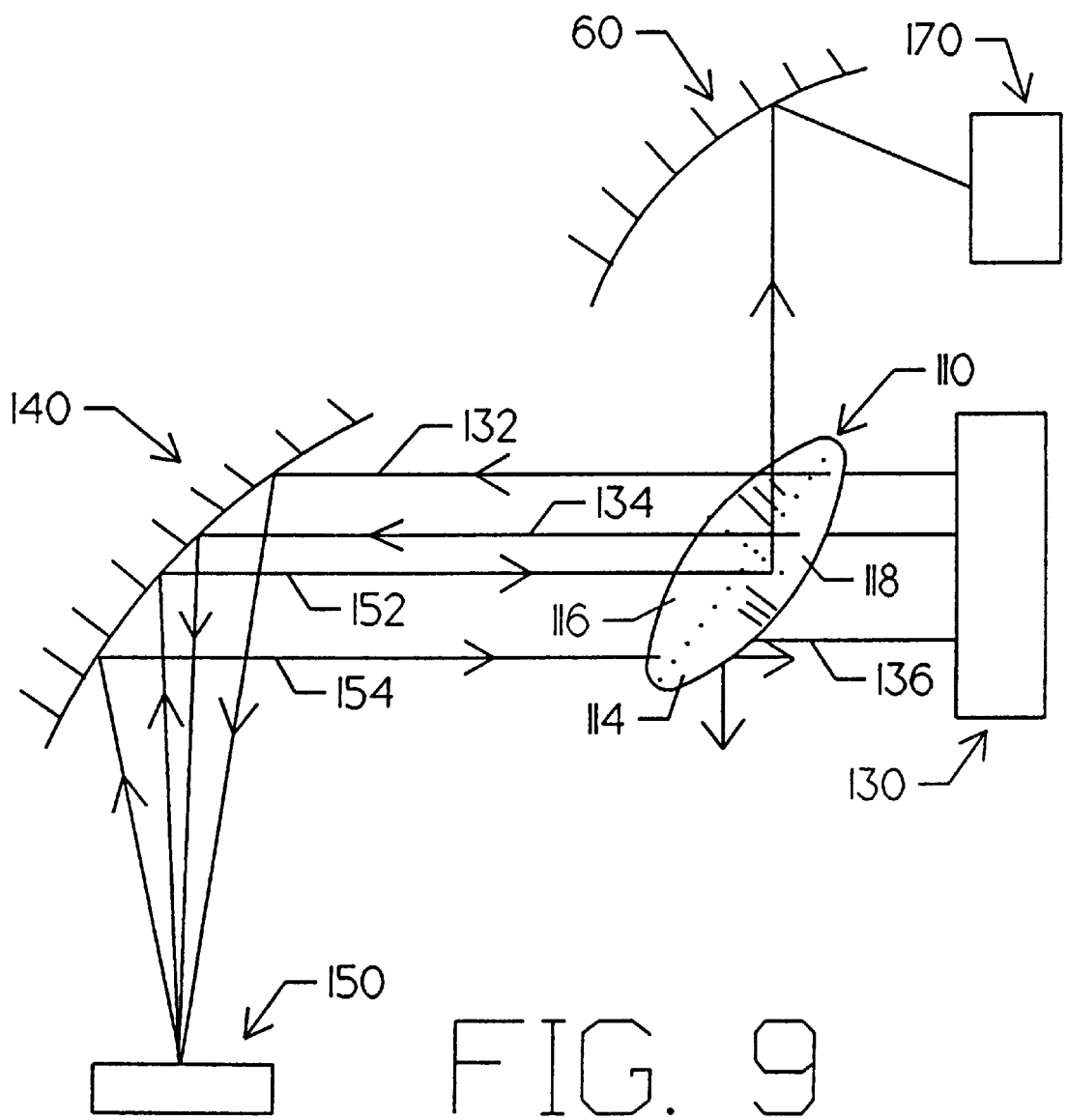
FIG. 9 is a schematic drawing showing the use of the specular control device of this invention in a spectroscopy system.

Referring now to FIG. 9, there is shown a schematic of a diffuse reflectance spectroscopy system utilizing the apparatus of this invention. A specular control device 110 is shown having open area 118 and reflective area 114. It is recognized that specular control device 110 need not be of a circular configuration as shown in FIGS. 8A and 8B but could be, for example, elliptical or rectangular in shape.

A light or energy source 130 is shown for providing an analytical source beam indicated at 132, 134 and 136. Source beam 132, 134 and 136 impinges on a first surface of specular control device 110. That portion of the source beam indicated at 136 is incident to reflecting portion 114 of specular control device 110 and is reflected away as shown by the arrow. That portion of the source beam indicated at 132 and 134 passes through open area 118 of specular control device 110, and continues on to be reflected by an elliptical mirror 140 to a desired focus on sample 150.

A diffuse reflectance beam 152 is reflected from sample 150 to mirror 140 and thence to the reflective surface 114 as shown by the arrows. Diffusely reflected beam 152 is reflected onto an elliptical mirror 60 from which it is focused into a detector 170 where the beam is analyzed.

In contrast to the diffusely reflected beam 152, a specularly reflected beam of light 154 is represented in FIG. 9. As is shown in FIG. 9, the specularly reflected beam 154 is reflected from the sample 150 to the mirror 140. This specularly reflected beam then passes through the open area 116 which is the open quadrant opposing the input quadrant 118 through which that light beam entered. The specularly reflected light 154 is thus not reflected to the analyzer 170 as described above for the diffusely reflected beam 152.

In FIG. 9, specular control device 110 could be a single element of the type generally known and having the reflective and open sections as shown in FIGS. 8A and 8B. Or, should it be desirable for manufacturing purposes, specular control device 110 could be a unit of a desired thickness having a first and second surface, each of which surface is treated in the same manner shown in FIGS. 8A and 8B. The reflecting and open sections on a first surface would be directly opposite the reflecting and open surfaces on a second surface to achieve the desired results.

Figure 10:
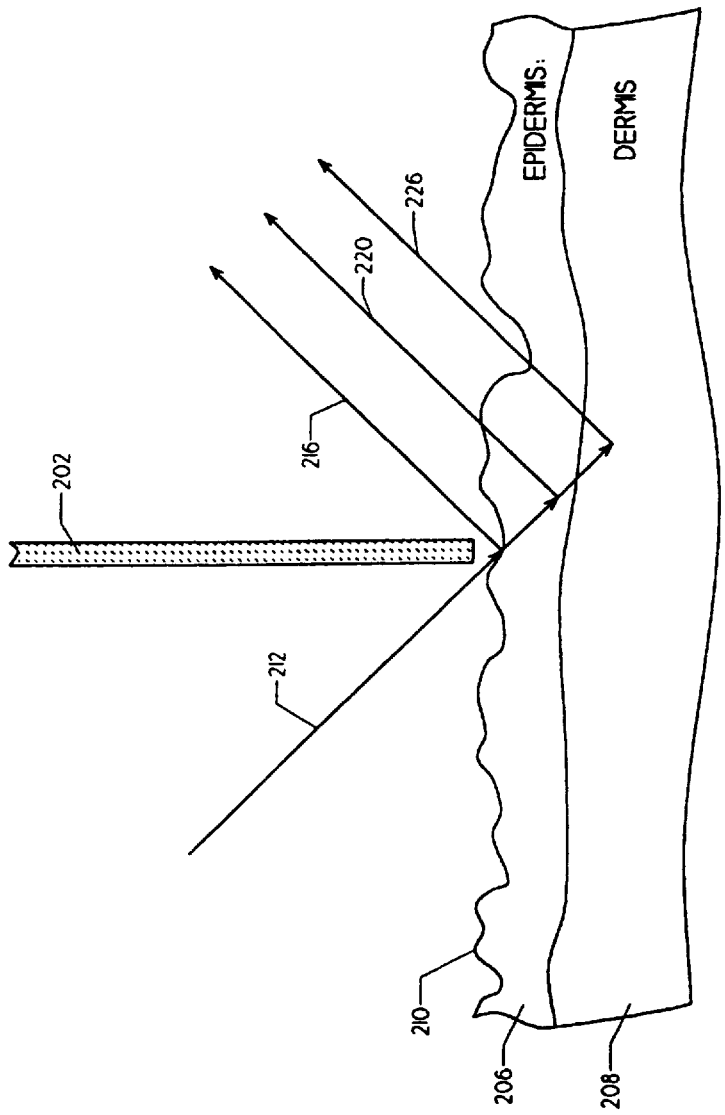
FIG. 10 is a schematic drawing showing a "thin" blocker blade for mechanically discriminating against specular reflectance, in accordance with the prior art.

FIG. 10 is a schematic drawing showing a "thin" blocker blade for mechanically discriminating against specular reflectance, in accordance with U.S. Pat. No. 4,661,706, issued Apr. 28, 1987, to Messerschmidt et al. Messerschmidt et al. demonstrate that the specular and the diffuse component of reflected light can be separated mechanically, taking advantage of the fact that the specular component emanates from the surface of the sample. A blade-like device, or blocker 202, "skims" the specular light before it can impinge on the detector.

Messerschmidt et al. teach that a "thin" blocker 202 is essential to maximize the efficiency of the system, and minimizing the distortion of the output spectrum. More particularly, Messerschmidt et al. state that to obtain the maximum efficiency and the closest approximation to the Kubelka-Munk relationship, a thin blocker device 202 should be used having a thickness that is a fraction of the optical depth of the sample. A thicker blocker, Messerschmidt et al. explain, will remove energy that penetrates only a short distance into the sample before reflecting, and thus may have a catastrophic effect on the efficiency when used with a sample having a shallow optical depth.

Messerschmidt et al. also state that a thick blocker may introduce spectral distortions caused by energy that is once reflected by the sample to the lower surface of the blocker and again reflected from the blocker to the sample before energy escapes from the far side of the blocker. This is problematic, according to Messerschmidt et al., because the energy reflected from the lower surface of the blocker will acquire the reflectance spectral features of the blocker itself and thus distort the output spectrum.

Applicants have discovered that the "thin" blocker approach of Messerschmidt et al. suffers from a number of limitations, some of which are discussed below. First, the "thin" blocker blade 202 does not provide any discrimination between the diffusely reflected energy that is reflected from various depths within the sample. That is, the thin blocker 202 does not provide any discrimination between the diffusely reflected light 220 reflected from a top layer and the diffusely reflected light 226 reflected from a lower layer, as shown.

This limitation is of particular importance when the tissue sample is layered or otherwise non-homogeneous, and only a selected set of the layers contain the desired information. This occurs in many applications including the non-invasive measurement of blood analytes, such as glucose, using the diffuse reflectance spectra reflected therefrom. For example, it is known that human skin has an outer epidermis layer 206 and a dermis layer 208. The epidermis layer 206 contains very little or no blood, and thus the corresponding diffusely reflected light 220 reflected from the epidermis layer 206 typically contains little or no glucose information. Applicants have discovered that the diffusely reflected light 220 from the epidermis layer 206 only contaminates the desired output spectrum 226 of the information rich dermis layer 208.

In addition to the above, the "thin" blocker 202 of Messerschmidt et al. may not perfectly conform to the rough surface 210 of the tissue sample. This can cause locations where the light 212 effectively leaks or pipes under the blocker 202 without interacting with the sample, thereby further contaminating the resulting output spectrum. This is shown explicitly by light ray 216.

Figure 11B:
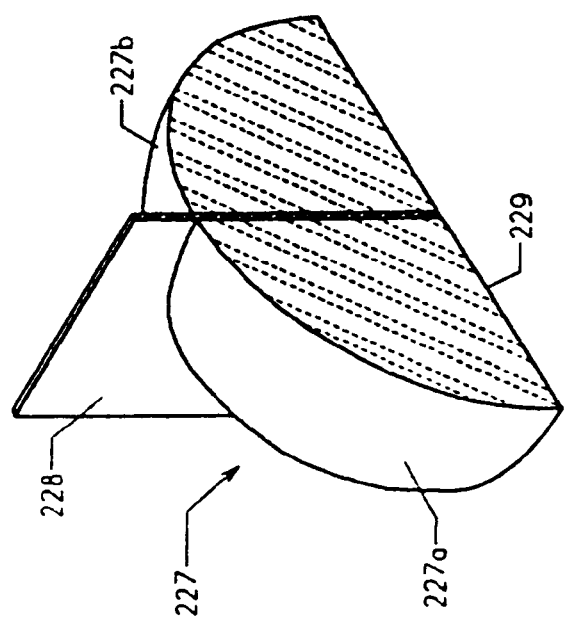
FIG. 11B is a cutaway view of the illustrative specular control device of FIG. 11A.
Figure 11A:
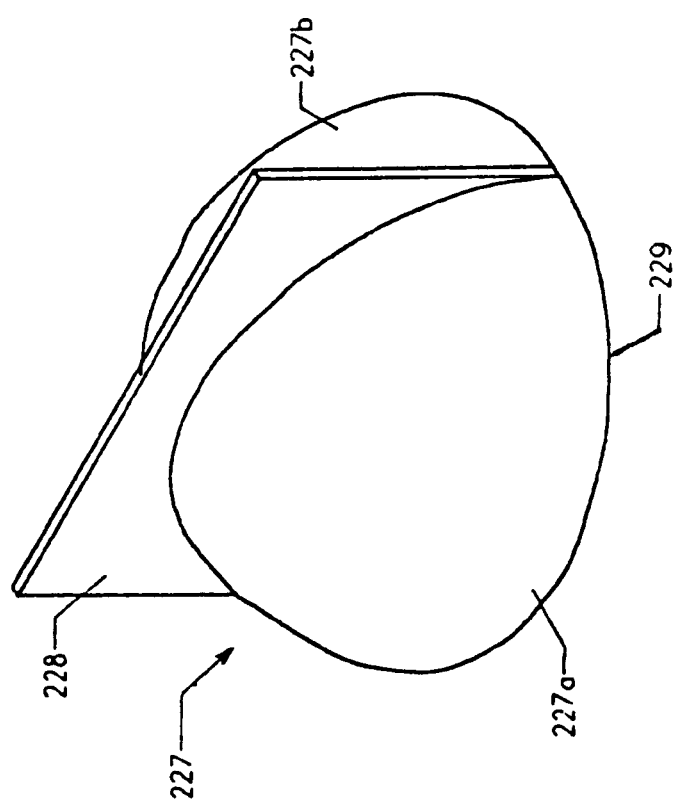
FIG. 11A is a perspective view of in illustrative specular control device in accordance with the present invention.

FIG. 11A is a perspective view of in illustrative specular control device in accordance with the present invention. FIG. 11B is a cutaway view of the same. The specular control device includes an immersion lens 227 that has a flat bottom surface 229 and a semi-circular shaped top surface. The flat bottom surface 229 is positioned on the surface of the tissue sample (not shown). A blocker blade 228 is positioned within the immersion lens, and extends substantially perpendicular to the surface of the tissue sample. The blocker blade 228 may divide the immersion lens into approximately two equal halves 227a and 227b, and extends downward to the flat bottom surface 229 of the immersion lens 227. The blocker blade 228 is constructed to either reflect or absorb light having a wavelength in the range of the expected specularly and diffusely reflected light.

The incident light is directed to one of the two equal halves 227a,227b of the immersion lens 227. The blocker blade 228 substantially prevents the incident light from traveling to the other half of the immersion lens 227. The immersion lens 227 directs the incident light to the tissue sample, and in some embodiments, focuses the light on an illuminated spot (see FIG. 15) on the surface of the tissue sample. A first portion of the incident light will typically be specularly reflected from the surface of the sample. A second portion of the light will typically enter the sample, and be diffusely reflected by the material within the sample. The diffusely reflected light is typically reflected by material that is at various depths within the sample.

Figure 12:
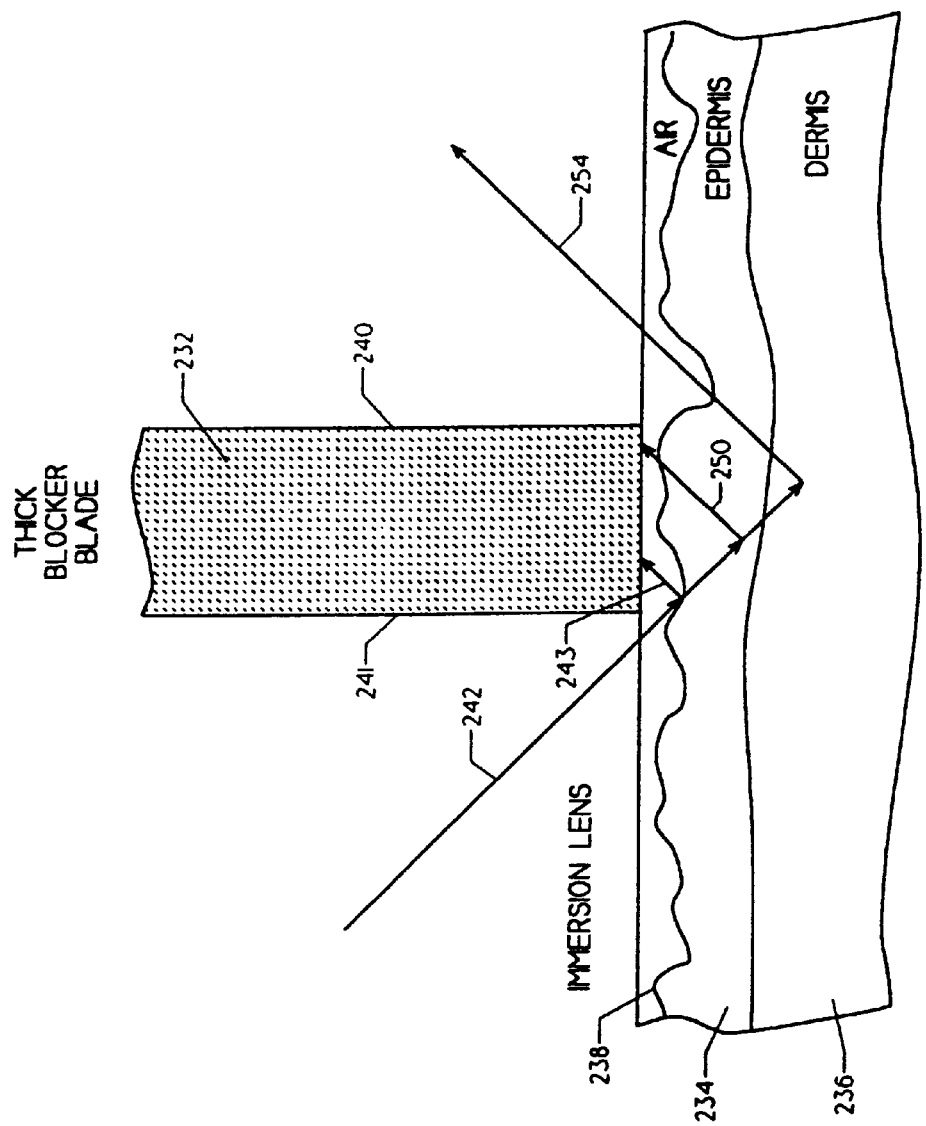
FIG. 12 is a simplified schematic drawing detailing the "thick" blocker blade of the present invention.

FIG. 12 is a simplified schematic drawing detailing the "thick" blocker blade of the present invention. The immersion lens is positioned adjacent the top surface 238 of a tissue sample. In the illustrative diagram, the tissue sample is human skin having an outer epidermis layer 234 and an inner dermis layer 236. Because the top surface 238 of the tissue sample is rough, gaps will typically be present between at least parts of the immersion lens and the top surface 238 of the tissue sample as shown.

In accordance with the present invention, a relatively thick blocker blade 232 is provided. The blocker blade 232 has a back surface 240 and a front surface 241, with a thickness defined therebetween. The tissue sample may include a number of layers, including an epidermis layer 234 and a dermis layer 236. Applicants have discovered that it is desirable to exclude the diffusely reflected light rays that are reflected by the epidermis layer.

To achieve discrimination, the back surface 240 of the blocker blade 232 is preferably laterally spaced a distance from the illuminated portion of the tissue sample such that the light rays 250 that are diffusely reflected from the epidermis layer 234 are substantially prevented from reaching the spectroscopic analyzer. As indicated above, the epidermis layer 234 may have little or no blood therein, and thus the diffusely reflected light from the epidermis layer 234 tends to contaminate the desired spectrum of the diffusely reflected light 254 from the information rich dermis layer 236. By preventing the diffusely reflected light 250 of the epidermis layer 234 from reaching the spectroscopic analyzer, a contaminated spectrum from the dermis layer 236 can be obtained and analyzed. The front surface 241 of the blocker blade 232 may be positioned directly adjacent the illuminated portion of the tissue sample, within the illuminated portion, or laterally spaced toward the back surface 240 relative to the illuminated portion.

The epidermis layer is typically about 40 micrometers to about 400 micrometers in thickness at desired sample areas. Applicants have found a preferred blocker blade thickness for these applications is 100 micrometers to 800 micrometers, with 400 micrometers most preferred.

In addition to the above, the thick blocker blade 232 of the present invention may substantially prevent the specularly reflected component 243 from reaching the spectroscopic analyzer, even when the surface of the sample is not perfectly flat as shown. Because the present invention provides a thick blocker blade 232, the leakage of light between the surface of the skin 238 and the blocker blade 232 may be reduced or eliminated. This may improve the quality of the resulting spectrum that is provided to the spectroscopic analyzer.

As can readily be seen, a method for obtaining a diffuse reflectance spectra from human tissue for the non-invasive measurement of blood analytes is contemplated. The method comprising the steps of: (a) generating infrared energy; (b) directing the infrared energy to the tissue; and (c) collecting the infrared energy that is reflected from a first depth and rejecting the infrared energy that is reflected from a second depth.

Figure 13:
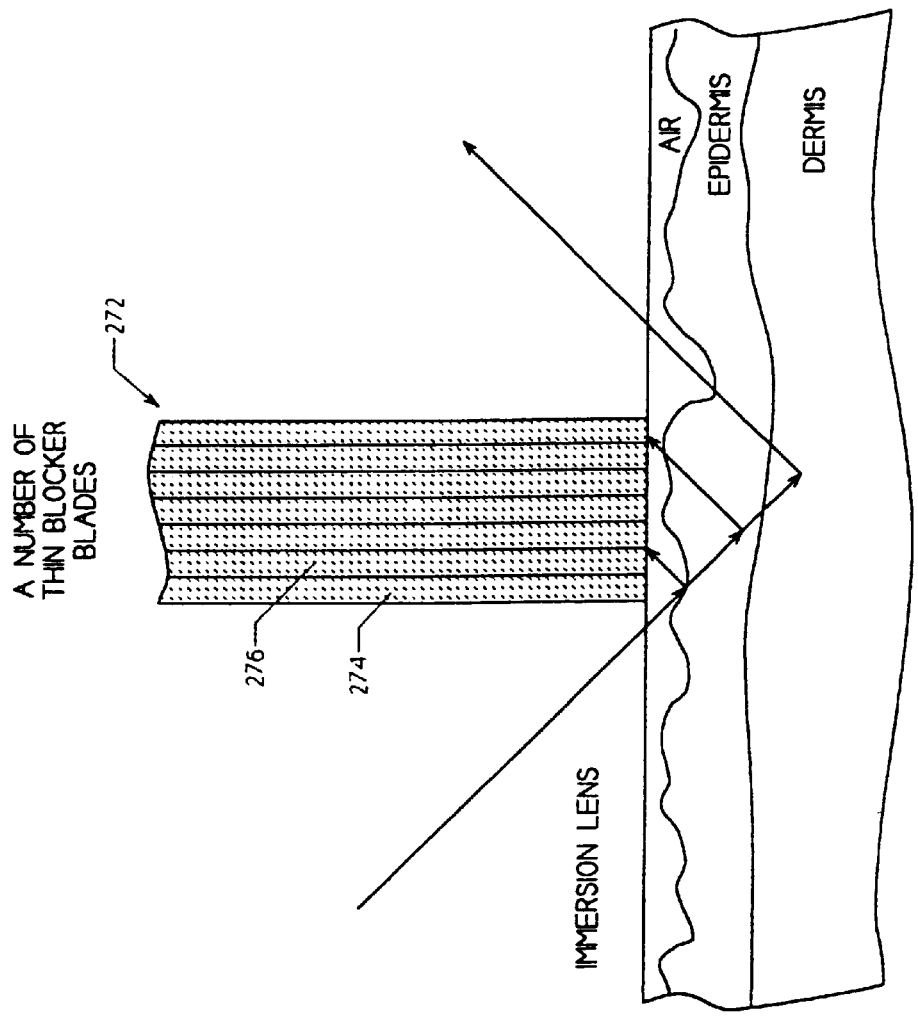
FIG. 13 is a simplified schematic drawing detailing the "thick" blocker blade of the present invention, made from a number of abutting thin blocker blades.

FIG. 13 is a simplified schematic drawing detailing the "thick" blocker blade of the present invention, made from a number of abutting thin blocker blades. Rather than forming the blocker blade 272 from a single homogeneous material, it is contemplated that a number of thin blocker blades, for example thin blocker blades 274, 276, may be used to form blocker blade 272.

Figure 14:
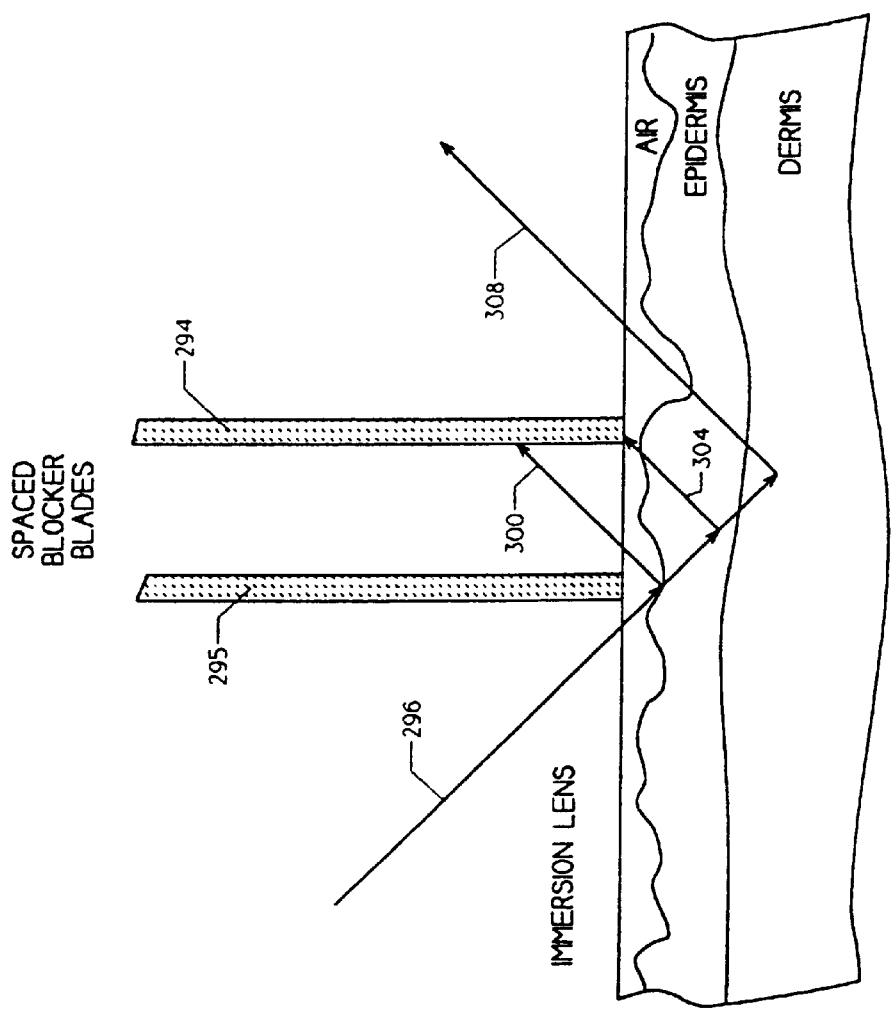
FIG. 14 is a simplified schematic drawing detailing an effectively "thick" blocker blade made from two spaced thin blocker blades.

FIG. 14 is a simplified schematic drawing detailing an effectively "thick" blocker blade made from two spaced thin blocker blades 294 and 295. In this illustrative embodiment, the front blocker blade 295 is used to confine the incident light 296 to the left portion of the immersion lens. The back blocker blade 294 is used to prevent both specularly reflected light 300, and any diffusely reflected light 304 that is reflected from the epidermis layer, from reaching the spectroscopic analyzer.

Figure 15:
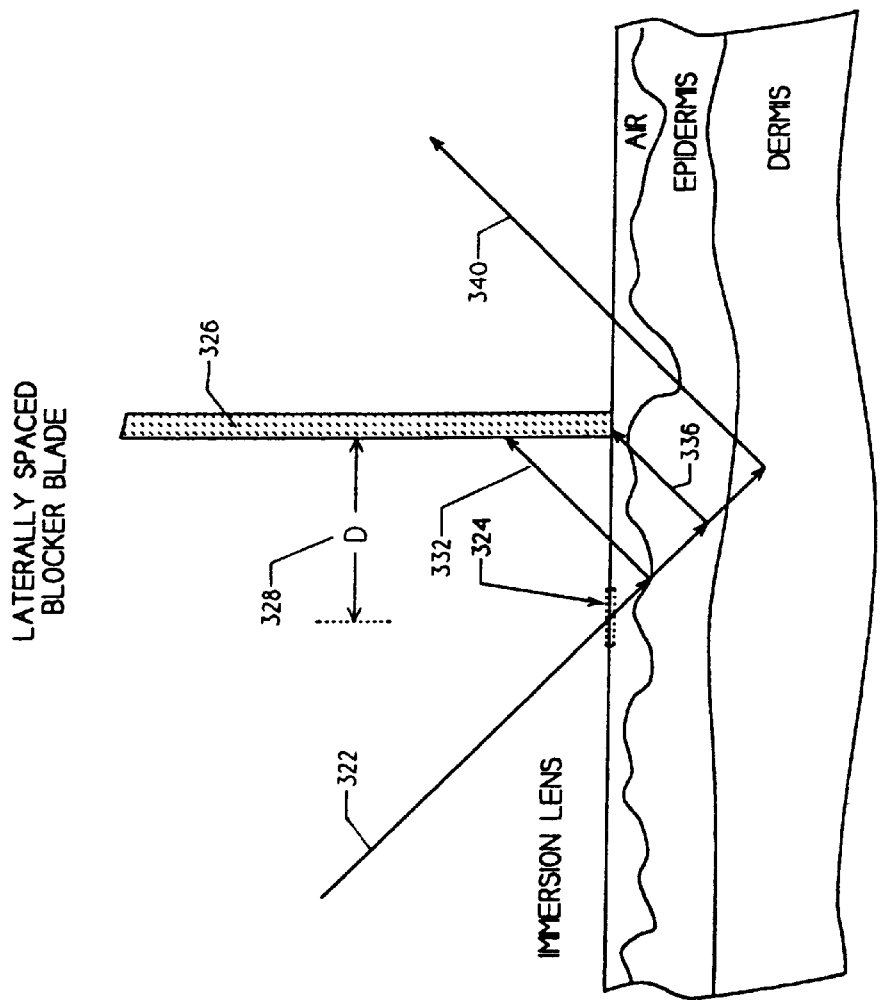
FIG. 15 is a simplified schematic drawing detailing an effectively "thick" blocker blade made from a single thin blocker blade that is laterally spaced from the illuminated spot of the incident light rays.

FIG. 15 is a simplified schematic drawing detailing an effectively "thick" blocker blade made from a single thin blocker blade that is laterally spaced from the illuminated spot of the incident light rays. As indicated above, the immersion lens may focus the incident light onto an illuminated spot 324. In this embodiment, no front blocker blade is needed to confine the incident light to the left portion of the immersion lens. Thus only one blocker blade is used, which is spaced a sufficient distance "D" 328 from the illuminated spot 324 to prevent both specularly reflected light 332 and any diffusely reflected light 336 provided by the epidermis layer, from reaching the spectroscopic analyzer.

Having thus described the preferred embodiments of the present invention, those of skill in the art will readily appreciate the other useful embodiments within the scope of the claims hereto attached.

What is claimed is:

1. An apparatus for obtaining a diffuse reflectance spectra from skin tissue for non-invasive measurement of analytes therein, the skin tissue having an epidermis layer and a dermis layer, the apparatus comprising:
    a source of infrared energy for generating and delivering infrared energy to a first location on the skin tissue;
    a collector for collecting infrared energy reflected from the dermis layer at a second location;
    means for causing the collector to collect primarily only the infrared light that is reflected from the dermis layer; and
    means for determining the concentration of a selected blood analyte by analyzing the infrared energy collected by the collector.

2. An apparatus as in claim 1, wherein the means for causing the collector to collect primarily only the infrared energy that is reflected from the dermis layer is positioned between the infrared energy source and the collector.

3. An apparatus as in claim 2, wherein the means for causing the collector to collect primarily only the infrared energy that is reflected from the dermis layer comprises a blocker.

4. An apparatus as in claim 3, wherein the blocker comprises a plate.

5. An apparatus as in claim 4, wherein the plate comprises a material opaque to infrared energy.

6. An apparatus as in claim 4, wherein the plate includes a front surface and a back surface, and wherein the back surface is laterally spaced from an illumination location to block infrared energy that is reflected from the epidermis layer.

7. An apparatus as in claim 6, wherein the front surface is positioned adjacent the illumination location.

8. An apparatus as in claim 6, wherein the front surface is laterally spaced from the illumination location.

9. An apparatus as in claim 6, wherein the plate is solid between the front surface and the back surface.

10. An apparatus as in claim 6, wherein the plate is not solid between the front surface and the back surface.

11. An apparatus as in claim 4, wherein the plate has a thickness, the infrared energy has a wavelength, and the thickness is greater than the wavelength.

12. An apparatus as in claim 11, wherein the thickness is greater than or equal to 100 micrometers.

13. An apparatus as in claim 11, wherein the thickness is 100 micrometers to 800 micrometers.

14. An apparatus for obtaining a diffuse reflectance spectra from skin tissue for non-invasive measurement of analytes therein, the skin tissue having an epidermis layer and a dermis layer, the apparatus comprising:
    a source of infrared energy for generating and delivering infrared energy to the skin tissue;
    a collector for collecting infrared energy reflected from the skin tissue;
    a blocker blade positioned between the infrared energy source and the collector such that the collector collects primarily only the infrared energy that is reflected from the dermis layer; and
    means for determining the concentration of a selected blood analyte by analyzing the infrared energy collected by the collector.

15. An apparatus for obtaining a diffuse reflectance spectra from skin tissue for non-invasive measurement of analytes therein, the skin tissue having an epidermis layer and a dermis layer, the apparatus comprising:
    a source of infrared energy for generating and delivering infrared energy to the skin tissue at an illumination location;
    a collector for collecting infrared energy reflected from the skin tissue;
    means for causing the collector to collect primarily only the infrared energy that is reflected from the dermis layer; and
    means for determining the concentration of a selected blood analyte by analyzing the infrared energy collected by the collector.

16. A method for obtaining a diffuse reflectance spectra from skin tissue for non-invasive measurement of analytes therein, the skin tissue having an epidermis layer and a dermis layer, the method comprising the steps of:
    generating infrared energy;
    directing the infrared energy to a first location on the skin tissue;
    selectively collecting only the infrared energy that is reflected from the dermis layer; and
    determining the concentration of a selected blood analyte by analyzing the collected infrared energy.

17. A method as in claim 16, wherein the infrared energy is collected from a second location spaced apart from the first location, and wherein only the infrared energy that is reflected from the dermis layer is present at the second location.

* * * * *